United States Patent [19]

Nelson

[11] 4,229,377

[45] * Oct. 21, 1980

[54] 2-DECARBOXY-2-HYDROXYMETHYL-16-FLUORO-PGE$_2$ COMPOUNDS

[75] Inventor: Norman A. Nelson, Galesburg, Mich.

[73] Assignee: The Upjohn Company, Kalamazoo, Mich.

[ * ] Notice: The portion of the term of this patent subsequent to Jun. 28, 1994, has been disclaimed.

[21] Appl. No.: 951,096

[22] Filed: Oct. 13, 1978

Related U.S. Application Data

[62] Division of Ser. No. 786,153, Apr. 6, 1977, Pat. No. 4,139,564, which is a division of Ser. No. 647,369, Jan. 8, 1976, Pat. No. 4,032,576.

[51] Int. Cl.$^3$ .......................................... C07C 177/00
[52] U.S. Cl. .................................................. 568/380
[58] Field of Search ..................................... 260/586 R

[56] References Cited

U.S. PATENT DOCUMENTS 4,032,576  6/1977  Nelson .................................. 260/586

*Primary Examiner*—Robert Gerstl
*Attorney, Agent, or Firm*—Robert A. Armitage

[57] ABSTRACT

This invention comprises certain analogs of the prostaglandins in which the C-1 carboxyl is replaced by a primary alcohol. Also provided in this invention are novel chemical processes useful in the preparation of the above prostaglandin analogs. These prostaglandin analogs exhibit prostaglandin-like activity and are accordingly useful for the same pharmacological purposes as the prostaglandins. Among these purposes are blood pressure lowering, labor induction at term, reproductive-cycle regulation, gastric antisecretory action, and the like.

1 Claim, No Drawings

2-DECARBOXY-2-HYDROXYMETHYL-16-FLUORO-PGE$_2$ COMPOUNDS

CROSS REFERENCE TO RELATED APPLICATIONS

The present application is a divisional application of U.S. Ser. No. 786,153, filed Apr. 6, 1977, issued as U.S. Pat. No. 4,139,564; which is a divisional application of U.S. Ser. No. 647,369, filed Jan. 8, 1976, issued as U.S. Pat. No. 4,032,576, on June 28, 1977.

The present invention is related to pharmacologically active 2-decarboxy-2-hydroxymethyl-16-fluoro-PGE$_2$ compounds whose preparation and use is described in U.S. Pat. No. 4,032,576, issued June 28, 1977, the relevant disclosure of which is hereby incorporated by reference.

I claim:

1. A prostaglandin analog of the formula

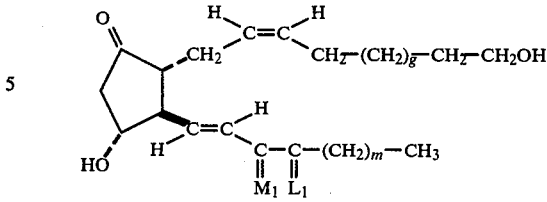

wherein M$_1$ is

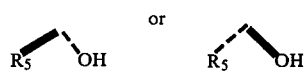

wherein R$_5$ is hydrogen or methyl;
wherein L$_1$ is

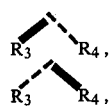

or a mixture of

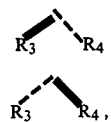

wherein R$_3$ and R$_4$ are hydrogen or fluoro, being the same or different;
wherein g is one, 2, or 3; and
wherein m is one to 5, inclusive:
with the proviso that at least one of R$_3$ and R$_4$ is fluoro.

* * * * *